United States Patent
Koyanagi

(10) Patent No.: US 9,726,569 B2
(45) Date of Patent: Aug. 8, 2017

(54) PIPING INSPECTION ROBOT AND METHOD OF INSPECTING PIPING

(71) Applicant: MOBILE ROBOT RESEARCH CO., LTD., Kamakura-shi, Kanagawa (JP)

(72) Inventor: Eiji Koyanagi, Yokosuka (JP)

(73) Assignee: MOBILE ROBOT RESEARCH CO., LTD., Kamakura-shi, Kanagawa (JP)

(*) Notice: Subject to any disclaimer, the term of this patent is extended or adjusted under 35 U.S.C. 154(b) by 222 days.

(21) Appl. No.: 14/653,844

(22) PCT Filed: Dec. 17, 2013

(86) PCT No.: PCT/JP2013/083725
§ 371 (c)(1),
(2) Date: Jun. 18, 2015

(87) PCT Pub. No.: WO2014/098068
PCT Pub. Date: Jun. 26, 2014

(65) Prior Publication Data
US 2015/0330860 A1 Nov. 19, 2015

(30) Foreign Application Priority Data
Dec. 18, 2012 (JP) .................... 2012-276238

(51) Int. Cl.
*G01M 3/24* (2006.01)
*G01M 3/18* (2006.01)
(Continued)

(52) U.S. Cl.
CPC .......... *G01M 3/005* (2013.01); *B25J 9/1679* (2013.01); *F16L 55/26* (2013.01); *F16L 55/32* (2013.01);
(Continued)

(58) Field of Classification Search
CPC .......... B08B 9/023; B08B 9/021; F16L 55/26; F16L 2101/30; G01M 3/246; G01M 3/18;
(Continued)

(56) References Cited

U.S. PATENT DOCUMENTS 4,331,034 A * 5/1982 Takeda ................. G01N 29/265
376/252
4,938,081 A * 7/1990 Negishi ................. F16L 55/28
73/865.8
(Continued)

FOREIGN PATENT DOCUMENTS

EP 0412396 A2 2/1991
JP 59-027455 2/1984
(Continued)

OTHER PUBLICATIONS

Extended European Search Report for the Application No. 13865231.8 (PCT/JP2013/083725), issued on Jul. 15, 2016, total 6 pages.
(Continued)

*Primary Examiner* — David A Rogers
(74) *Attorney, Agent, or Firm* — Masuvalley & Partners

(57) ABSTRACT

Provided is an inspection robot that is self-propelled on piping, measures moisture contained in a lagging material using a mounted inspection device, for example, a neutron moisture meter, and detects risk of corrosion. The inspection robot includes a main frame 1 including a recessed part 17 fit onto an outer circumferential surface of piping P, a main frame drive mechanism (first drive mechanism) D1 that causes the main frame to advance/retract in an axis direction of the piping, a revolving member 32 supported in an advanceable/retractable manner along an arc-shaped locus in the recessed part of the main frame, a revolving member drive mechanism (second drive mechanism) D2 that moves
(Continued)

the revolving member, and an inspection device mounted on the revolving member.

9 Claims, 11 Drawing Sheets

(51) Int. Cl.
| | |
|---|---|
| G01M 3/00 | (2006.01) |
| B25J 9/16 | (2006.01) |
| F16L 55/26 | (2006.01) |
| F16L 55/32 | (2006.01) |
| G01N 23/00 | (2006.01) |
| G01N 27/82 | (2006.01) |
| G01N 29/04 | (2006.01) |
| G01N 23/02 | (2006.01) |
| F16L 101/30 | (2006.01) |

(52) U.S. Cl.
CPC ........... *G01N 23/00* (2013.01); *G01N 23/005* (2013.01); *G01N 23/025* (2013.01); *G01N 27/82* (2013.01); *G01N 29/04* (2013.01); *F16L 2101/30* (2013.01); *G01N 2223/613* (2013.01); *G01N 2223/628* (2013.01); *G01N 2291/269* (2013.01); *Y10S 901/02* (2013.01); *Y10S 901/19* (2013.01)

(58) Field of Classification Search
CPC .......... G01M 3/243; G01N 2291/2634; G01N 2291/2636
See application file for complete search history.

(56) References Cited

U.S. PATENT DOCUMENTS

| | | | | |
|---|---|---|---|---|
| 5,069,234 | A * | 12/1991 | Nielsen | B08B 9/023 118/307 |
| 5,267,417 | A * | 12/1993 | Rose | B24C 1/086 451/38 |
| 5,361,791 | A * | 11/1994 | Chapman | B08B 9/023 134/122 R |
| 5,385,609 | A * | 1/1995 | Rose | B24C 3/32 118/119 |
| 5,398,461 | A * | 3/1995 | Rose | B24C 3/32 15/104.04 |
| 5,458,683 | A * | 10/1995 | Taylor | B08B 9/023 118/307 |
| 5,698,854 | A * | 12/1997 | Gupta | G01N 23/18 250/358.1 |
| 7,059,945 | B2 * | 6/2006 | Skinner | B24C 1/08 118/307 |
| 7,178,418 | B2 * | 2/2007 | Richter | F16L 55/26 137/15.07 |
| 7,458,289 | B2 * | 12/2008 | Houldey | F16L 55/28 324/219 |
| 7,656,997 | B1 | 2/2010 | Anjelly | |
| 8,141,442 | B2 * | 3/2012 | Roberts | F17D 5/00 73/865.8 |
| 9,389,150 | B2 * | 7/2016 | Kimpel, Jr. | G01M 99/00 |
| 9,400,263 | B2 * | 7/2016 | An | G01N 29/225 |
| 9,415,426 | B1 * | 8/2016 | Blake | B08B 9/023 |
| 2010/0275694 | A1 * | 11/2010 | Roberts | F17D 5/00 73/637 |
| 2014/0156067 | A1 * | 6/2014 | An | G01N 29/225 700/245 |

FOREIGN PATENT DOCUMENTS

| | | | |
|---|---|---|---|
| JP | 05139292 | A * | 6/1993 |
| JP | 07-181171 | A | 7/1995 |
| JP | 07-191001 | A | 7/1995 |
| JP | 08-285717 | A | 11/1996 |
| JP | 10-292893 | A | 11/1998 |
| JP | 2006-126022 | A | 10/2004 |
| JP | 2006-184029 | A | 7/2006 |
| JP | 2008-215815 | A | 9/2008 |
| JP | 2010-203525 | A | 9/2010 |
| JP | 2011-027559 | A | 2/2011 |

OTHER PUBLICATIONS

IB Authorized Officer Yukari Nakamura, International Preliminary Report on Patentability in International Application No. PCT/JP2013/083725, issued on Jul. 2, 2015 total 11 pages with English translation.

* cited by examiner (a) (Contact position)

(b) (Lifted position)

PIPING INSPECTION ROBOT AND METHOD OF INSPECTING PIPING

RELATED APPLICATIONS

This application is the U.S. National Phase of and claims priority to International Patent Application No. PCT/JP2013/083725, International Filing Date Dec. 17, 2013, entitled Pipe Inspection Robot, And Method For Inspection Of Pipe, which claims benefit of Japanese Patent Application No. JP2012-276238, filed Dec. 18, 2012, both of which are incorporated herein by reference in their entireties.

TECHNICAL FIELD

The present invention relates to a self-propelled piping inspection robot that inspects existence or non-existence of damage of piping, and a method of inspecting piping.

BACKGROUND ART

Piping installed in various plants and used for transferring fluids such as a liquid, powder, and gas has a structure in which an outer surface of a steel-made pipe body is covered with a heat insulating material (lagging material) and a protective iron sheet in order.

As a technique to inspect abnormality of the pipe body such as damage, deterioration, and fluid leakage, many methods to directly insert inspection equipment into an inside of the pipe body and perform an inspection have been conventionally proposed. However, in the methods to perform an inspection from the inside of the pipe body, it is difficult to find occurrence positions of corrosion and damage occurring on the outer surface of the pipe body, and of pipe wall thinning, holes, and cracks due to the corrosion and damage, and the existence or non-existence of fluid leakage.

Especially, it is difficult to directly visually observe and find the abnormality that occurs on the pipe body covered with the lagging material and the like. Therefore, methods to indirectly detect the abnormality from an outside using change of the humidity and the amount of moisture as a clue have been proposed.

For example, Patent Literature 1 (Japanese Patent Application Laid-Open No. 08-285717) proposes a system in which a humidity sensor is provided in a rapture-assumed position of piping, and which detects leakage at an initial stage of the leakage.

Patent Literature 2 (Japanese Patent Application Laid-Open No. 10-292893) proposes a water leakage detection device provided with a water leakage saucer outside piping, and which detects accumulated water leakage.

Patent Literature 3 (Japanese Patent Publication No. 4763632) proposes a method of measuring the moisture contained in the lagging material in which a neutron moisture meter is arranged outside piping.

The piping is arranged in a position where a worker cannot easily approach, such as a high place or a narrow place. Further, the worker may not be able to come close to the piping in order to avoid risk of radiation exposure, and a work time in the vicinity of the piping may be restricted, in a piping facility of a nuclear power station and the like.

As a technique to non-destructively inspect (flaw detection) the piping in a position where the worker cannot approach, Patent Literature 4 (Japanese Patent Application Laid-Open No. 2006-184029) proposes a method to extend an inspection arm from a self-propelled robot that travels on the ground to access the piping.

Patent Literature 5 (Japanese Patent Application Laid-Open No. 2006-126022) proposes a method to operate the inspection arm by hand.

However, the method to access and inspect the piping from the ground may be restricted due to arrangement of other structural objects in the vicinity of the piping to be inspected or risk of the work environment, and the like, and in this case, the techniques disclosed in Patent Literatures 4 and 5 cannot handle the inspection.

Therefore, the inventor of the present invention has proposed a self-propelled robot that perform an inspection using the piping itself as a supporting body, as Patent Literature 6 (Japanese Patent Application Laid-Open No. 2010-203525).

However, an inspection cart described in Patent Literature 6 is self-propelled in a state of being installed on an upper half of cylindrical piping and detects only the upper half of the piping, and is self-propelled in a state of being installed on a lower half of the piping and detects only the lower half of the piping. Therefore, it is necessary to individually inspect the piping by dividing a predetermined length range into the upper half and the lower half, and thus workability of the inspection and inspection efficiency are low.

That is, when inspecting a lower portion of the outer surface of the piping, a device body as a heavy load including a neutron moisture meter becomes in a state of being hung on the lower portion of the piping using only the arm, and thus it is necessary to enhance the strength of the arm. Therefore, it is necessary to configure configuration parts such as a traveling device in a complicated and strong manner, and the heavy load at the piping side becomes large and an operation needs time.

CITATION LIST

Patent Literature

Patent Literature 1: Japanese Patent Application Laid-Open No. 08-285717
Patent Literature 2: Japanese Patent Application Laid-Open No. 10-292893
Patent Literature 3: Japanese Patent Publication No. 4763632
Patent Literature 4: Japanese Patent Application Laid-Open No. 2006-184029
Patent Literature 5: Japanese Patent Application Laid-Open No. 2006-126022
Patent Literature 6: Japanese Patent Application Laid-Open No. 2010-203525

SUMMARY OF INVENTION

Technical Problem

The present invention has been made in view of the foregoing, and an objective is to provide a piping inspection robot that can inspect the entire outer surface without omission including the lower half of the piping while being set to the upper half of the outer surface of the piping and self-propelled, in non-destructive inspection of the damage, corrosion and the like of the piping, and the existence or non-existence of the abnormality, from an outside of the piping, and a method of inspecting piping using the piping inspection robot.

As means for measuring the mount of moisture in the lagging material in the piping with the outer surface covered with the lagging material and a metal thin film in order by a non-destructive method, a neutron moisture meter is suitable.

As another means for detecting (inspecting, checking) the abnormality of the entire piping from the outside, regardless of the existence or non-existence of the lagging material, a magnetic inspection device, an ultrasonic inspection device, and an X-ray inspection device can be exemplified.

The present invention has a configuration in which a frame including a semicircular recessed portion is included, and the neutron moisture meter can be revolved around the piping in a state where a main body with a lower portion open is placed on an upper portion of the piping, whereby a device configuration can be simplified and the entire device can be decreased in weight, and mobility and operability are improved. Since the lower portion is open, the robot can pass through a portion where the T-shaped stand that supports a lower portion of the piping exists.

Solution to Problem

To achieve the objective, a piping inspection robot according to the invention of first aspect is a piping inspection robot that is placed on an outer circumferential surface of piping and is advanceable/retractable in an axis direction of the piping, and inspects existence or non-existence of abnormality of the piping, the piping inspection robot including: a main frame including a recessed part to be fit onto the outer circumferential surface of the piping; a main frame drive mechanism that advances/retracts the main frame in the axis direction of the piping; a revolving member supported in a advanceable/retractable manner along an arc-shaped locus in the recessed part of the main frame; a revolving member drive mechanism that moves the revolving member; and an inspection device mounted on the revolving member.

The invention of second aspect is the piping inspection robot, wherein the inspection device is configured to be freely advanceable/retractable in a direction intersecting with a moving direction of the revolving member.

The invention of third aspect is the piping inspection robot, wherein the main frame drive mechanism includes a movable base pivotally supported in a freely revolvable manner in a direction intersecting with a moving direction of the main frame, by a portion of the main frame corresponding to a central position of the recessed part, a movable base drive mechanism that changes a revolution angle of the movable base, a pair of traveling wheels supported by the movable base in a freely rotatable manner, and a wheel drive mechanism that rotates and drives the traveling wheels, and the pair of traveling wheels is arranged symmetrically with respect to a shaft portion of the movable base as a center.

The invention of fourth aspect is the piping inspection robot, wherein the movable base is pivotally supported in a freely revolvable manner by the shaft portion perpendicular to a tangential line assumed on the outer circumferential surface of the piping facing the central position of the recessed part.

The invention of fifth aspect is the piping inspection robot, wherein the wheel drive mechanism includes a travel motor mounted on the movable base, a driven gear supported by the movable base in a freely rotatable manner, and which receives transmission of drive force from an output gear of the travel motor, and universal joints respectively coupled with both end portions of a rotating shaft of the driven gear, and the wheel drive mechanism is coupled with shaft end portions of the traveling wheels through the universal joints.

The invention of sixth aspect is the piping inspection robot, wherein the inspection device is any of a moisture measuring device including a neutron moisture meter, an ultrasonic flaw detection device, a magnetic flaw detection device, and an X-ray flaw detection device.

The invention of seventh aspect is the piping inspection robot, wherein the drive mechanisms are remotely operated by wireless or wire communication. The invention of eighth aspect is a method of inspecting piping using the piping inspection robot according to first aspect, the method including: a setting process of fitting the recessed part onto the piping outer surface; a process of measuring existence or non-existence of abnormality of the piping by the inspection device; a process of moving the inspection device in a circumferential direction of the piping and measuring the existence or non-existence of abnormality of each portion of the piping of the circumferential direction; and a process of moving the inspection device in an axis direction of the piping. The invention of ninth aspect is the method of inspecting piping according to eighth aspect using the moisture measuring device as the inspection device, the method causing the moisture measuring device to come close to the piping at a time of measurement, and causing the moisture measuring device to be separated from the piping at a time of non-measurement.

Advantageous Effects of Invention

The piping inspection robot of the present invention has a configuration in which a frame including a semicircular recessed portion is included, and a measuring device can be revolved around the piping in a state where a main body with a lower portion open is placed on an upper portion of the piping, whereby the device configuration can be simplified and the entire device can be decreased in weight, and the mobility and the operability can be improved. Since the lower portion is open, the robot can pass through a portion where the T-shaped stand that supports the lower portion of the piping exists.

DESCRIPTION OF EMBODIMENTS

Hereinafter, a piping inspection robot according to an embodiment of the present invention will be described in detail with reference to the appended drawings.

Figure 1:
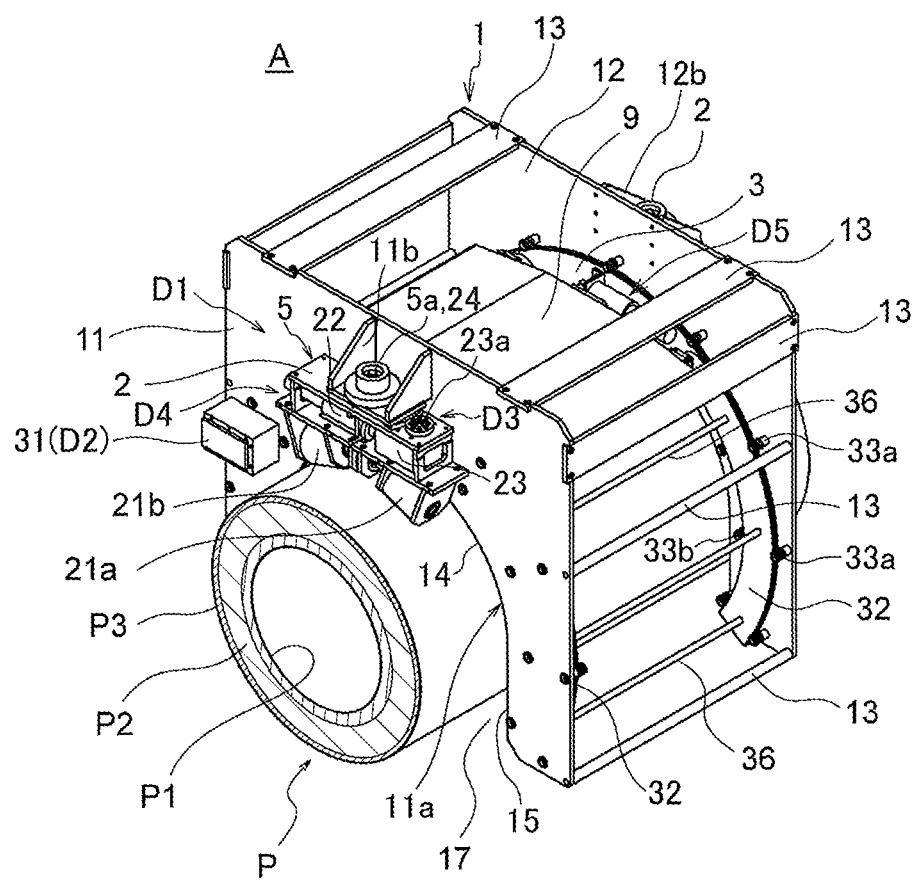
FIG. 1 is a perspective view of a piping inspection robot mounted on piping.
Figure 2:
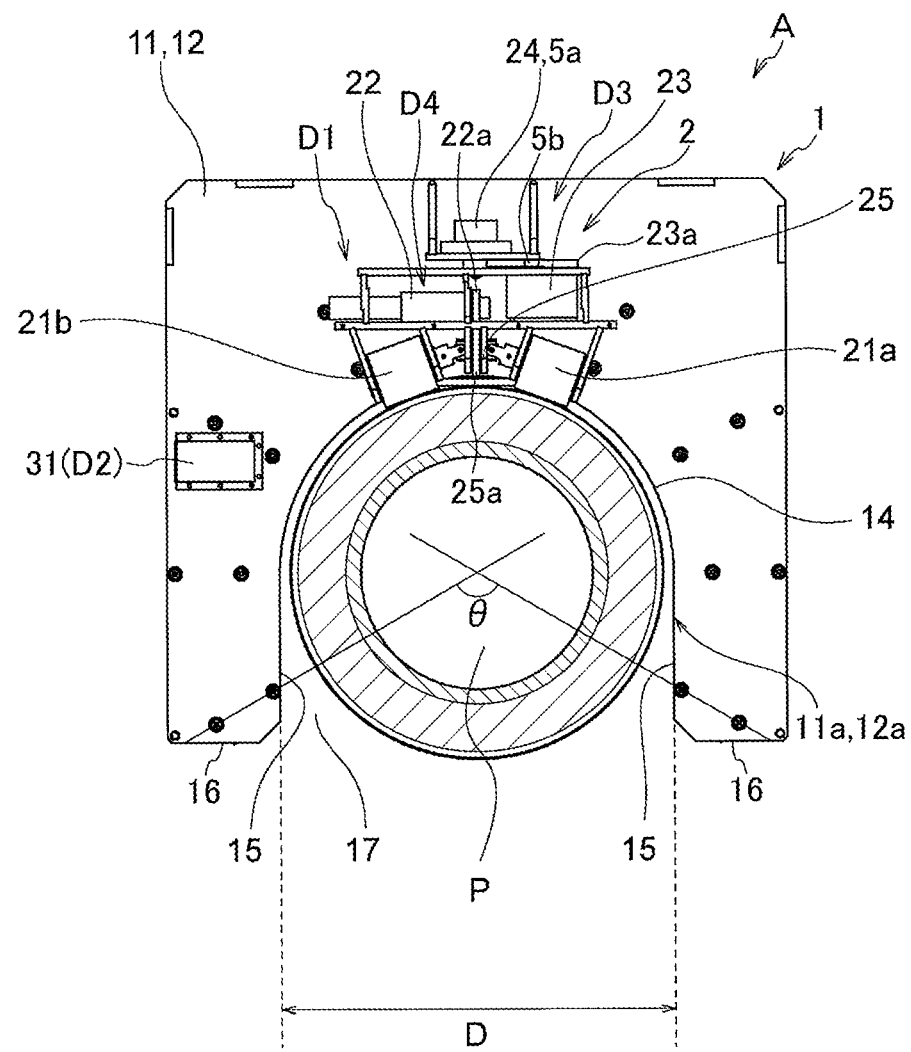
FIG. 2 is a front view of the piping inspection robot mounted on the piping.
Figure 3:
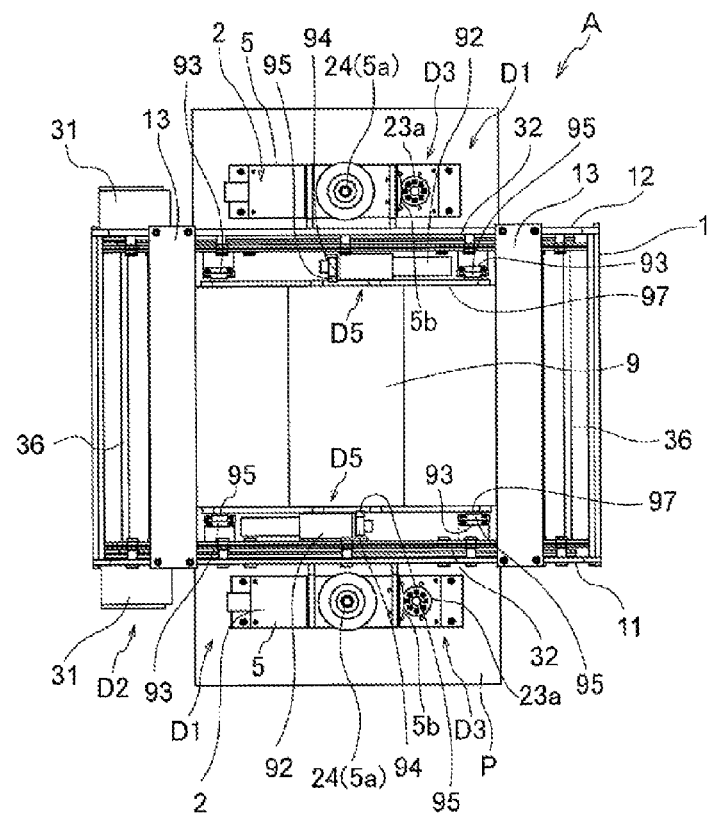
FIG. 3 is a plan view of the piping inspection robot mounted on the piping.
Figure 4:
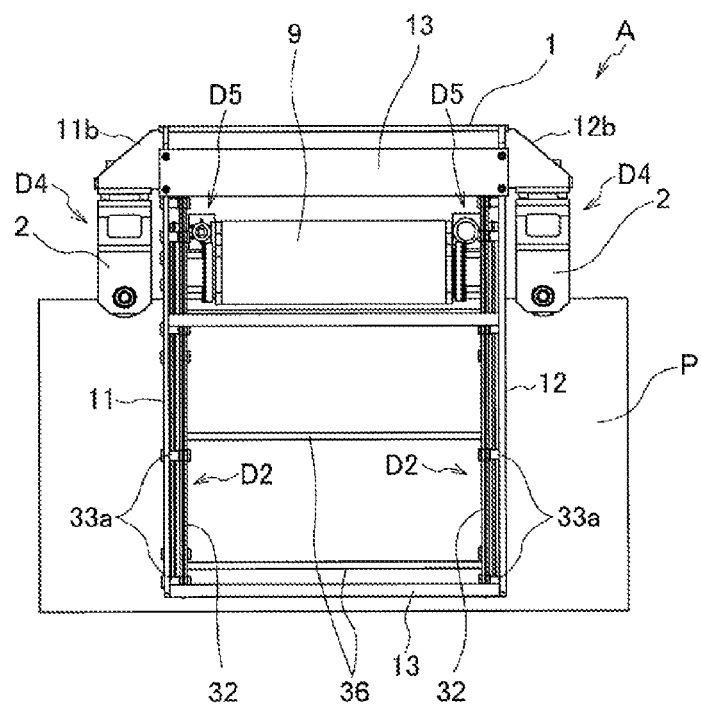
FIG. 4 is a side view of the piping inspection robot mounted on the piping.
Figure 5:
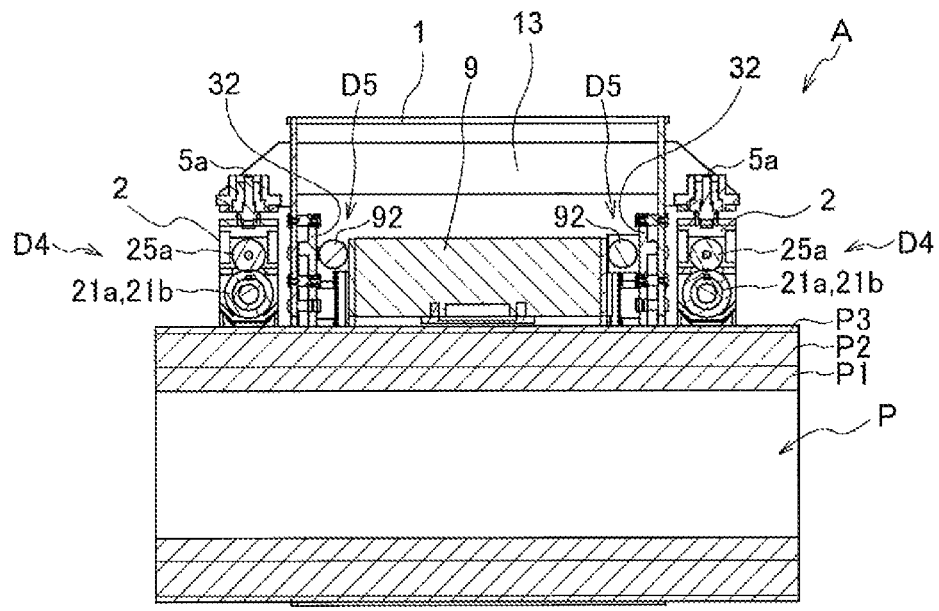
FIG. 5 is a vertical cross-sectional view of the piping inspection robot mounted on the piping.
Figure 6:
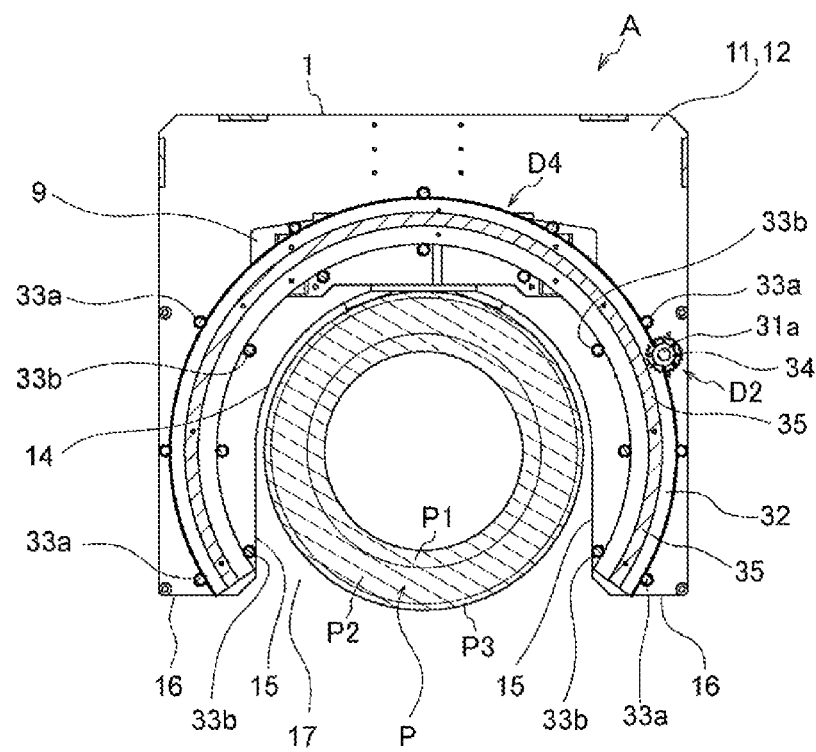
FIG. 6 is a cross-sectional view of a principal part of the piping inspection robot mounted on the piping.
Figure 7:
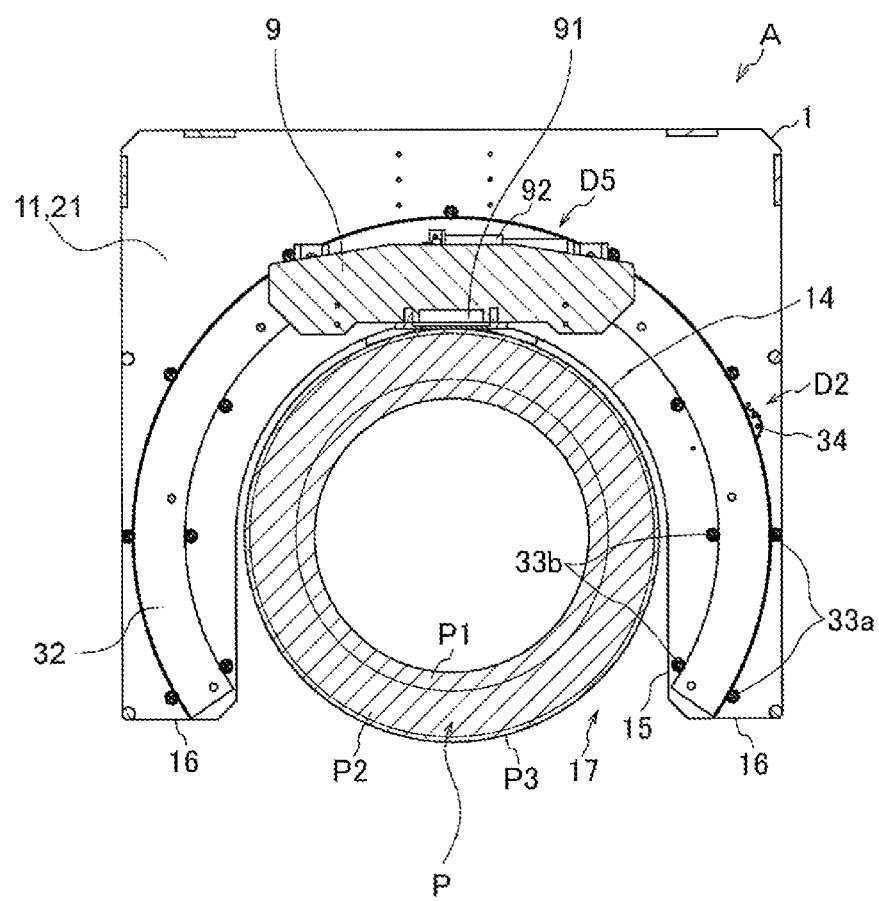
FIG. 7 is a vertical cross-sectional view of a central position of the piping inspection robot mounted on the piping.
Figure 8:
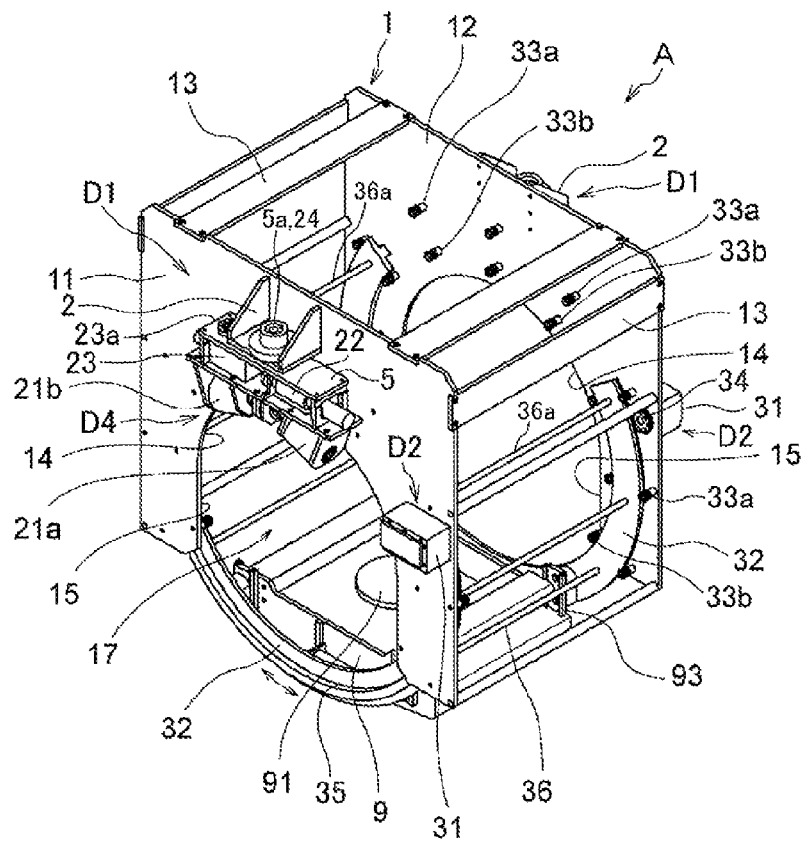
FIG. 8 is a perspective view of the piping inspection robot in a state where a moisture measuring device (inspection device) is in a lower position.
Figure 9:
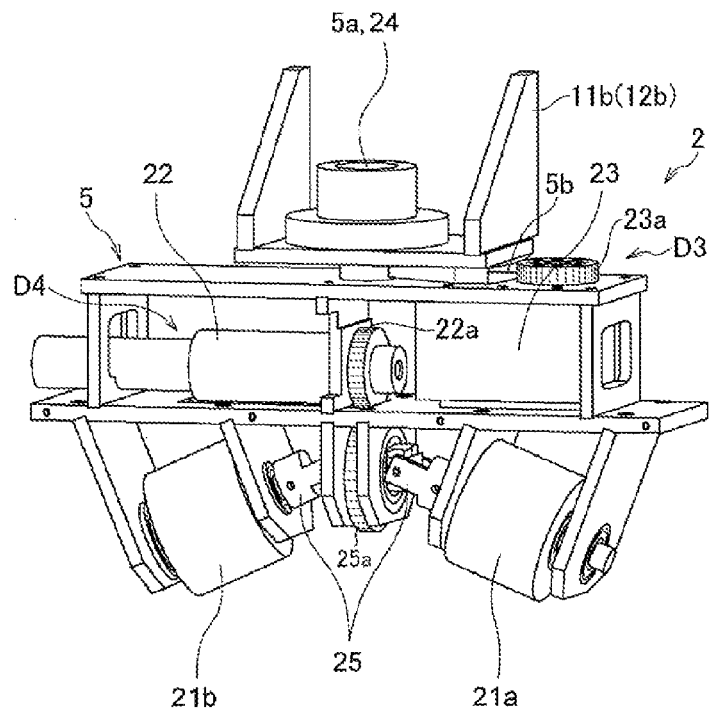
FIG. 9 is a perspective view illustrating a traveling device of the piping inspection robot.
Figure 10:
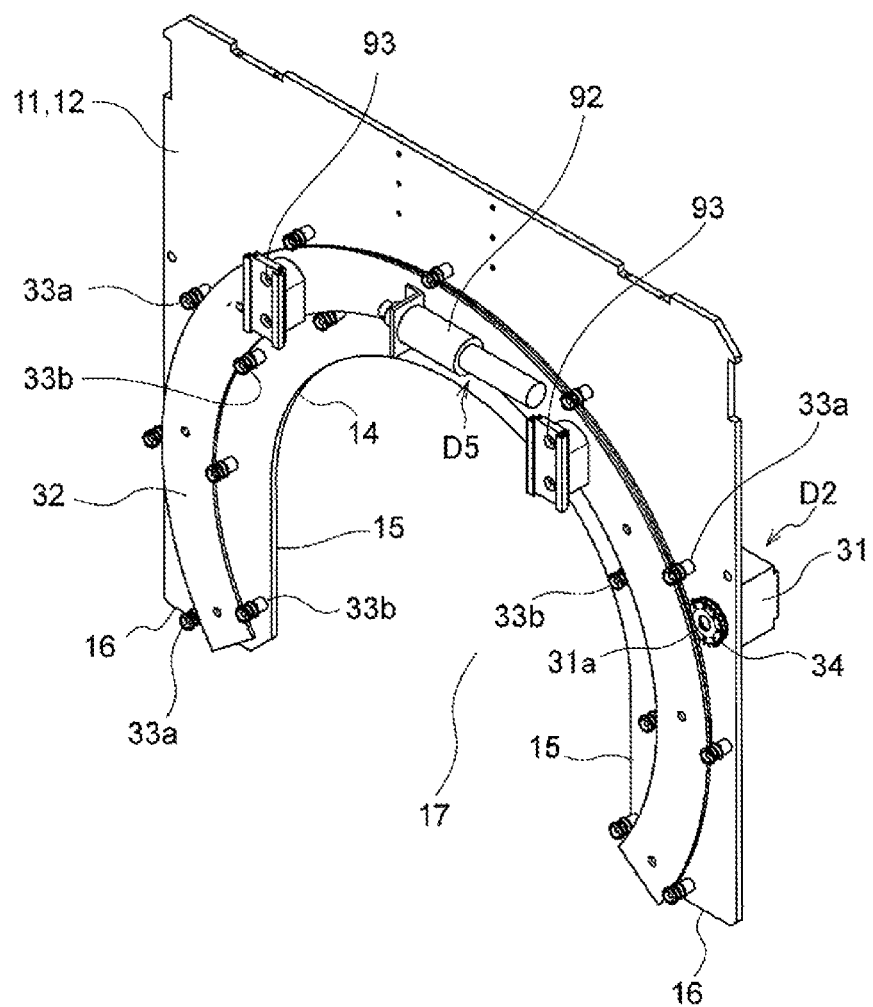
FIG. 10 is a perspective view illustrating a revolving member drive mechanism (upper position) of the piping inspection robot.
Figure 11:
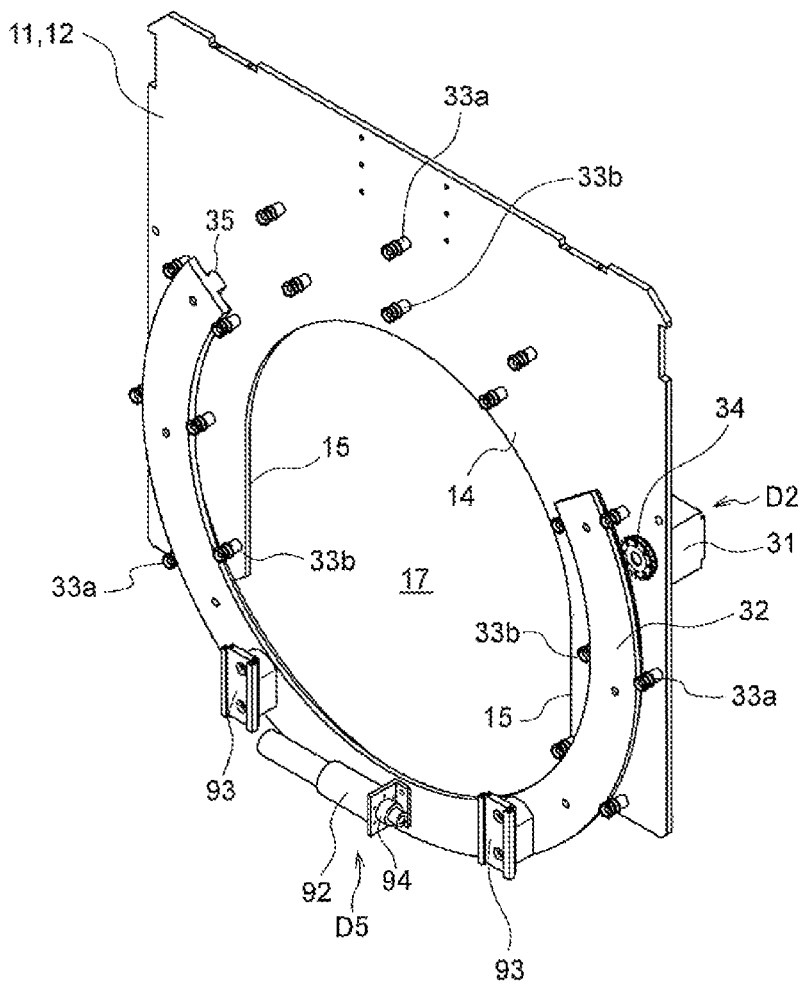
FIG. 11 is a perspective view of a revolving member drive mechanism (lower position) of the piping inspection robot.
Figure 12:
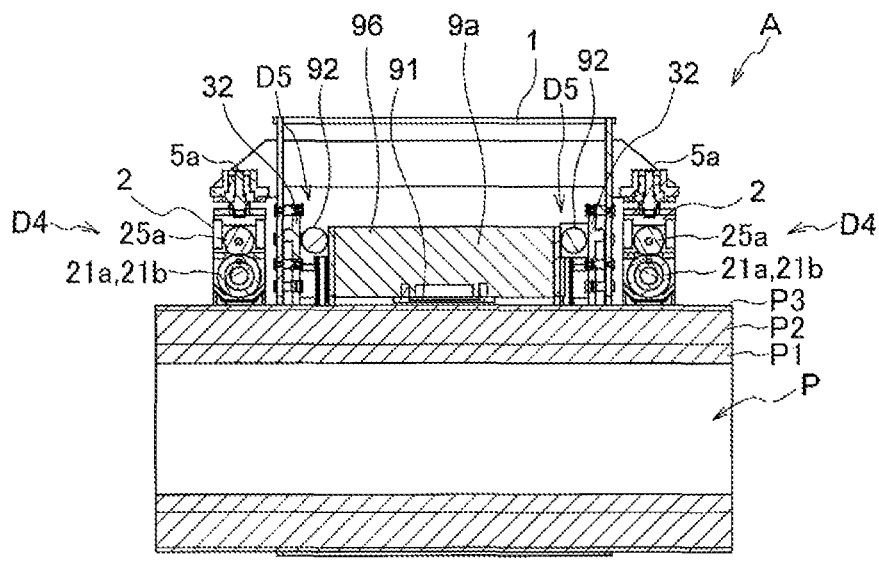
FIGS. 12 (*a*) and 12 (*b*) are vertical cross-sectional views of side parts of the moisture measuring device in lifted and lowered states, and FIG. 12(*a*) illustrates a lowered (piping contact) position and FIG. 12 (*b*) illustrates an lifted position.
Figure 12:
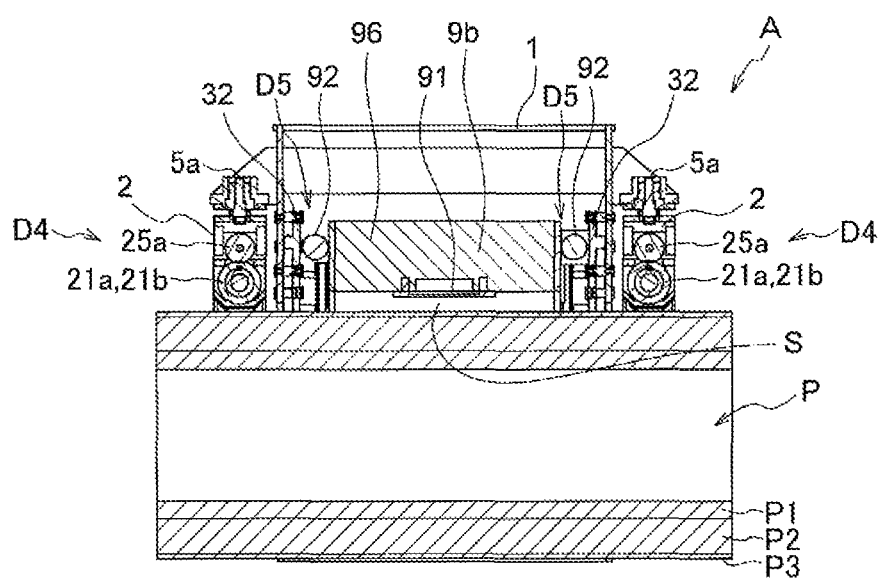

FIG. 1 is a perspective view of a piping inspection robot according to an embodiment of the present invention mounted on piping, FIG. 2 is a front view of the piping inspection robot, FIG. 3 is a plan view of the piping inspection robot, FIG. 4 is a side view of the piping inspection robot, FIG. 5 is a vertical cross-sectional view of the piping inspection robot, FIG. 6 is a cross-sectional view of a principal part of the piping inspection robot, FIG. 7 is a vertical cross-sectional view of a central position of the piping inspection robot, FIG. 8 is a perspective view of the piping inspection robot in a state where a moisture measuring device (inspection device) is in a lower position, FIG. 9 is a perspective view illustrating a traveling device of the piping inspection robot, FIG. 10 is a perspective view illustrating a revolving member drive mechanism (upper position) of the piping inspection robot, FIG. 11 is a perspective view of a revolving member drive mechanism (lower position) of the piping inspection robot, and FIGS. 12(*a*) and 12 (*b*) are vertical cross-sectional views of side parts of the moisture measuring device in lifted and lowered states, and FIG. 12(*a*) illustrates a lowered (piping contact) position and FIG. 12(*b*) illustrates an lifted position.

A piping inspection robot A according to the present invention is means mounted to embrace an outer surface of a piping P, self-propelled in an axis direction (longitudinal direction) on the outer surface of the piping, and which detects corrosion, damage, and the like occurring on the outer surface of the piping, and other abnormality, with an mounted inspection device.

As the inspection device, various inspection devices (flaw detection devices) such as an inspection device that detects the abnormality based on the amount of moisture, the humidity, and the like, an inspection device that detects the abnormality according to change of magnetism, an inspection device that detects the abnormality with ultrasonic waves, and an inspection device that detects the abnormality with an X ray are applicable.

In embodiments below, a case of using a moisture measuring device (neutron moisture meter) as an example of the inspection device will be described.

Note that the piping here refers to piping including a heat insulating material surrounding the piping although it may refer to a metal pipe body itself.

The piping inspection robot A according to the present embodiment is means that detects and notifies existence or non-existence of corrosion, wear, and other damage, and risk of fluid leakage of a piping P, by measuring the moisture contained in a lagging material P2 that covers the outer surface of the piping, using a mounted moisture measuring device 9.

As illustrated in FIG. 1 and the like, the piping P has a configuration in which the outer circumferential surface of a pipe P1 that is a metal-made steel pipe is covered with the lagging material P2 having heat insulating properties, and an outer surface of the lagging material is covered with a covering material P3 of a thin steel sheet or the like. The covering material P3 is often fixed by seam assembling with a steel sheet, and a joint portion of the seam assembling is protected with a seal member or the like. However, the sealed portion is deteriorated due to aged deterioration or application of external force, and rainwater and sea fog penetrates into the lagging material P2. Therefore, when the moisture contained in the lagging material P2 is increased, the corrosion advances from the outer surface of the steel pipe, the wall of the steel pipe becomes thin, and a pin hole becomes an opening, and cool/warm water and the like cannot be safely supplied. The piping P may sometimes be arranged at a high place where a worker cannot easily reach, or may be arranged in a complicated manner, in a plant, a power station, or a nuclear power facility. Further, approach to the piping is difficult in an accident site of such a facility.

The piping inspection robot A includes a recessed part (lower open part) to be stably set (fit) into the outer surface of the piping P in a state of covering the outer surface of the piping P from above, and not only can be moved in the axis direction of the piping in a state where the recessed part is fit onto the piping outer surface from above, but also can go around along the outer circumferential surface of the piping at an arbitrary position of the piping. Therefore, the piping inspection robot can inspect the entire outer circumferential surface of the piping in high work efficiency, by simply being set on the piping once, while the device configuration can be simplified, and the device can be decreased in weight.

An object to be inspected by the piping inspection robot according to the present invention is piping in which the lagging material such as a heat insulating material is wound around the outer circumferential surface of a metal pipe body of a steel pipe, and the surface thereof is covered with a thin steel sheet or the like. For this kind of piping, it is difficult to find the abnormality such as corrosion of the outer surface of the main pipe body only with a visual check from the outer surface.

Meanwhile, a main cause of the corrosion of the outer surface of the metal pipe body is the amount of moisture contained in the lagging material. Therefore, to accurately determine the existence or non-existence of the corrosion, detection of the amount of moisture contained in the lagging material is important. Further, when a fluid transferred in the piping causes leakage through a corroded portion or damaged portion of the piping, the leaked fluid becomes a liquid, and may penetrate into the lagging material. Therefore, occurrence of the corrosion and the like can be recognized by detection of an increase in the amount of the liquid.

First, an overall configuration of the piping inspection robot will be described.

As illustrated in the perspective view of FIG. 1, the piping inspection robot A is means placed on the outer circumferential surface of the piping P, and which detects the existence or non-existence of the abnormality while advancing/retracting (moving) in the axis direction of the piping.

The piping inspection robot A roughly includes a main frame 1 including a recessed part 17 having a shape that is fit onto the outer circumferential surface of the piping P (an inner surface shape that is approximately matched with the outer circumferential surface of the piping), a main frame drive mechanism (first drive mechanism) D1 that causes the main frame 1 to advance/retract in the axis direction of the piping P, an arc-shaped revolving member 32 supported in an advanceable/retractable manner along an arc-shaped moving locus in the recessed part 17 of the main frame 1, a revolving member drive mechanism (second drive mechanism) D2 that moves the revolving member 32, and a moisture measuring device (inspection device) 9 moved along an inner circumferential edge of the recessed part 17 by the revolving member 32.

The main frame 1 roughly includes a front frame plate 11 having an approximately arc-shaped (approximately semi-circular) recessed portion 11a that configures the recessed part 17 in a lower edge central portion, a rear frame plate 12 arranged behind, being separated from, and in parallel to the front frame, and having an approximately arc-shaped (approximately semicircular) recessed portion 12a that configures the recessed part 17, and a plurality of beam materials 13 that couples both of the frame plates 11 and 12.

The recessed portions 11a and 12a that configure the recessed part 17 include semicircular (arc-shaped) recessed portions 14 positioned at upper portions, and linear portions 15 linearly extending downward from both end edges of the arc-shaped recessed portions 14.

Traveling devices 2 are respectively installed on outer surface portions corresponding to central portions (center portions) of the arc-shaped recessed portions 14 of the front frame plate 11 and the rear frame plate 12.

The revolving member drive mechanisms (second drive mechanisms) D2 respectively including the arc-shaped revolving members 32 that can be reciprocatively revolved along inner surfaces of the recessed parts, that is, along the arc-shaped recessed portions 14, are respectively provided in inner side surfaces of the front frame plate 11 and the rear frame plate 12. The revolving members 32, which are configured in an arc-shaped manner such that a part of an annular body made of a belt-like metal thin film is cut, are driven by drive motors 31 respectively provided in the frame plates 11 and 12, and are integrally moved along a circumferential locus. Note that a range of the arcs of the revolving members 32 is an angle $\theta+\alpha$ or more, and 360 degrees$-(\theta-\alpha)$ or less. The angle is made by two linear lines that connect right and left guide rolls provided at lowermost portions of the frame plates 11 and 12, of guide rolls 33a and 33b described below, and an approximately center of the piping P. Here, $\alpha$ defines an amount of protrusion to cause the revolving members not to fall out of the guide rolls, and is about 10 degrees in the present embodiment. Therefore, the arcs of the revolving members 32 are favorably from 180 to 250 degrees, both inclusive. That is, the range of the arcs of the revolving members is set to $\theta+\alpha$ or more, whereby the revolving members 32 are prevented from falling out of the guide rolls 33a and 33b when being rotated. Further, the range is set to 360 degrees$-(\theta-\alpha)$ or less, whereby the revolving members 32 are put out of the way when the piping inspection robot A is placed on the outer circumferential surface of the piping P. In the case of the arrangement of the guide rolls 33a and 33b illustrated in FIG. 2, $\theta$ is about 120 degrees.

The moisture measuring device 9 is attached to a position around an intermediate part of the revolving members 32 that are arranged to face each other. A neutron moisture meter that configures the moisture measuring device 9 measures the moisture in a state of being in contact with (close to) the outer surface of the piping. When the main frame 1 is moved in the axis direction, or when the revolving members are moved in the circumferential direction, the neutron moisture meter is separated from the surface of the piping and is caused to be in a retracting state.

The piping inspection robot A is configured to be remotely operated by wire or wireless means so as to be controlled from a remote position.

When the moisture measuring device 9 is used as the inspection device, the piping inspection robot A is suitable for a check of the piping arranged in a horizontal direction. This is because the moisture held in the lagging material is moved by gravity, but the moisture is less likely to be moved in the longitudinal direction of the piping in the case where the piping is arranged in the horizontal direction.

Next, configuration elements of the piping inspection robot A will be described.

(1) Main Frame

The main frame 1 configures a device body frame of the piping inspection robot A. An overall configuration of the main frame 1 is illustrated in the perspective views of the piping inspection robot in FIGS. 1 and 8. A front, a plane, a side, and the like are illustrated in other drawings.

The main frame 1 illustrated in FIGS. 1 and 8 is configured such that the front and rear frame plates 11 and 12 are coupled with a few beam materials 13, and is integrated in a frame manner. A lower side of the main frame 1 is open, and serves as the recessed part 17 that is a space into which the piping P is inserted. The moisture measuring device 9 is arranged inside the main frame 1. The moisture measuring device 9 is mounted in the revolving members 32 attached to the inner surface sides of the front and rear frame plates 11 and 12. The beam materials 13 are arranged at positions where the beam materials 13 do not interfere with operations (moving loci) of the revolving members 32 and of the moisture measuring device 9.

As illustrated in the front view of FIG. 2, the arc-shaped recessed portions 14 are provided in the same positions of the front and rear frame plates 11 and 12 having an approximately the same shape. The linear portions 15 extend downward continuously from the both end edges of the arc-shaped recessed portions 14. Lower ends 16 of the front and rear frame plates 11 and 12 are positioned lower than the center of the piping P fit in the recessed part 17 (stability in a placed state is secured). The recessed part 17 is formed by the arc-shaped recessed portion 14 and the linear portion 15 continuing therefrom. An open width D of the recessed part 17 (arc-shaped recessed portion 14) is set to be slightly larger than the diameter of the piping P. The shape of the recessed part 17 including the open width D is designed according to a specification of the piping P.

The arc-shaped recessed portions 14 of the present embodiment are configured as semi-arc-shaped recessed portions. However, the arc-shaped recessed portions 14 do not necessarily have the semi-arc shape (an angle of 180 degrees in the circumferential direction), and may have an angle of less than 180 degrees.

The traveling devices 2 are respectively attached to appropriate places (the outer surfaces in the present example) of the frame plates 11 and 12, the places corresponding to the central positions of the arc-shaped recessed portions 14 in the circumferential direction. Further, the drive motors 31 of the revolving member drive mechanisms D2 are attached to other portions of the frame plates 11 and 12.

Two lines of the guide rolls 33a and 33b that guide the revolving members 32, which advance/retract along the arc-shaped moving loci, are arranged inside the front and rear frame plates 11 and 12, having an interval nearly corresponding to the width of the revolving members. The guide rolls 33a and 33b are configured from a plurality of guide rolls 33a arranged along an outer circumferential edge of the revolving members 32, and a plurality of guide rolls 33b arranged along inner circumferential edges.

The respective guide rolls 33a and 33b may be rolls as rotating members pivotally supported in a freely rotatable manner by pins installed on the inner surfaces of the frame plates 11 and 12 in a protruding manner, or may be non-rotation rolls made of a low friction material.

As illustrated in FIGS. 6, 10, and the like, rotating shafts (output shafts) 31a of the drive motors 31 penetrate the frame plates 11 and 12 into the insides of the frame plates, and shaft centers of drive gears 34 are fixed to the respective rotating shafts 31a. The drive gear 34 includes a rack gear 35 on the outer circumferential surface. The drive gear 34 meshes with the rack gear 35 formed along the longitudinal direction of the revolving member 32 to transmit drive force from the motor, and causes the revolving member 32 to advance/retract along the arc-shaped moving locus (which is formed between the guide roll lines). To be specific, the revolving member 32 can be moved while being revolved between an upper position illustrated in FIG. 10 and a lower position illustrated in FIG. 11.

The revolving member 32 is configured to advance/retract along the circular moving locus along an inner circumferential surface (the arc-shaped recessed portion 14 and the linear portion 15) of the recessed part 17, and when the revolving member 32 is positioned at the upper position illustrated in FIG. 6, both end portions of the revolving member is terminated in the vicinity of the lower ends 16 at the both sides of the frame.

Note that the widths of the both end portions of the revolving member 32 are made narrower than other portions, whereby the lower end portions can smoothly enter a position between the guide rolls 33a and 33b when one end portion of the revolving member is moved from one lower end 16 to the other lower end 16 via the recessed part at the time of revolution of the revolving member.

As illustrated in FIG. 6 and the like, the rack gear 35 meshing with the drive gear 34 is provided on the outer surface of the revolving member 32 along the longitudinal direction (circumferential direction). Further, as illustrated in FIGS. 3, 8, and 10, guides 93 that are guide rails to guide the moisture measuring device 9 and a lifting and lowering motor 92 that lifts the moisture measuring device are installed on the revolving member 32. A part to be guided that is guided by the guides 93 in a freely slidable manner is provided on the outer surface of the moisture measuring device 9, and is driven by the lifting and lowering motor 92 and guided in a direction coming close to the piping outer surface, and in a direction being separated from the piping outer surface in a freely advanceable/retractable manner. FIG. 6 illustrates a state in which the revolving member drive mechanism D2 including the revolving member 32 is attached on the inner surface of the frame plate 11. FIG. 11 illustrates a state in which the revolving member 32 is revolved by 180 degrees from the state of FIG. 10. The revolving member 32 may be revolved and returned in a reverse direction after being revolved by 180 degrees, or may be revolved by 180 degrees or more in the same direction if it is configured such that a plurality of drive motors 31 is provided and any of the drive gears 34 of the drive motors 31 always meshes with the rack gear 35 of the revolving member 32, or if a plurality of drive gears 34 is provided so that the drive gears 34 of the drive motor 31 always mesh with the rack gear 35 of the revolving member 32 even if there is a single drive motor 31. A length in the circumferential direction of the revolving member 32 is set to a length sufficiently exceeding the angle θ+α or more, and favorably 180 degrees. The angle is made by the two linear lines that connect the right and left guide rolls provided at the lowermost portions, and an approximate center of the piping P. Accordingly, the revolving members are prevented from falling out of the open portion between the lower ends 16. Note that, when there is no concern about falling out of the open portion, the length in the circumferential direction of the revolving member may be set to 180 degrees or less.

An output gear 94 of the lifting and lowering motor 92 is caused to mesh with a rack gear 95 provided on the outer surface of the moisture measuring device 9, whereby the moisture measuring device 9 can be caused to come close to the piping side or can be lifted or lowered (advanced/retracted) to be separated from the piping, by rotation of the output gear 94 (FIG. 3).

(2) Traveling Device

The traveling devices 2 are installed at the outer surface sides of the front and rear frame plates 11 and 12.

The first drive mechanism (main frame drive mechanism) D1, which configures the traveling device 2, is means that causes the main frame 1 to advance/retract in the axis direction of the piping P.

The first drive mechanism D1 includes a movable base 5 pivotally supported in a revolvable manner by a shaft portion 5a extending in a direction (a radial direction of the arc-shaped recessed portion 14) intersecting with the moving direction (the axis direction of the piping) of the main frame, by a portion of the main frame 1 corresponding to a central position of the recessed part 17 (arc-shaped recessed portion 14) in the circumferential direction as illustrated in FIG. 9, a movable base drive mechanism (third drive mechanism) D3 that changes a revolution angle of the movable base 5, a pair of traveling wheels 21a and 21b, which are independently supported by the movable base 5 in a freely rotatable manner, and a wheel drive mechanism (fourth drive mechanism) D4 that rotates and drives the traveling wheels 21a and 21b. That is, the first drive mechanism D1 includes the movable base 5 pivotally supported in a freely revolvable manner in the direction intersecting with the moving direction (the axis direction of the piping) of the main frame, by the portion of the main frame 1 corresponding to the central position of the recessed part 17, the movable base drive mechanism (third drive mechanism) D3 that changes the revolution angle of the movable base 5, the pair of traveling wheels 21a and 21b supported by the movable base in a freely rotatable manner, and the wheel drive mechanism (fourth drive mechanism) D4 that rotates and drives the traveling wheels, and the pair of traveling wheels is arranged symmetrically with respect to the shaft portion 5a of the movable base as a center.

Further, the movable base 5 is pivotally supported in a freely revolvable manner by the shaft portion 5a perpendicular to a tangential line assumed on the outer circumferential surface of the piping that faces the central position of the recessed part 17.

The pair of traveling wheels 21a and 21b is arranged symmetrically with respect to the shaft portion 5a of the movable base 5 as a center. The movable base 5 is revolved in the horizontal direction in FIG. 1 and the like, so that the traveling wheels can be revolved in the same direction.

The movable base drive mechanism D3 includes a steering motor 23 mounted on the movable base that is revolved in the horizontal direction around the shaft portion 5a (steering shaft 24) provided in fixed members 11b and 12b fixed to the frame plates 11 and 12, and a movable base driven gear 5b integrated with the movable base 5, and operated by meshing with an output gear 23a, a shaft center of which is fixed to an output shaft of the steering motor.

The steering shaft (shaft portion 5a) 24 is set to be operable in a revolution range of about ±7° by the steering motor 23. This is provided to correct a phenomenon in which the piping inspection robot A is moved being gradually inclined in the circumferential direction from an uppermost portion of the piping due to waviness or bending of the piping P, even if the traveling wheels 21a and 21b are similarly driven.

The steering motor 23 is driven and the output gear 23a is revolved forwardly or reversely by a command from control means (a controlling device, not illustrated), so that the movable base 5 (the traveling wheels 21a and 21b) can be revolved in the horizontal direction around the shaft portion 5a through the movable base driven gear 5b.

The wheel drive mechanism (fourth drive mechanism) D4 that rotates and drives the traveling wheels 21a and 21b includes a travel motor (self-propelled motor) 22 mounted on the movable base 5, constant velocity joints 25 that transmit the drive force from the travel motor to the respective traveling wheels, and the traveling wheels 21a and 21b provided right and left and coupled with the respective constant velocity joints.

That is, the fourth drive mechanism D4 includes the travel motor 22 mounted on the movable base 5, the driven gear 25a supported by the movable base in a freely rotatable manner, and which receives transmission of drive force from an output gear 22a of the travel motor, and the constant velocity joints 25 (universal joints) respectively coupled with both end portions of a rotating shaft of the driven gear, and is configured to be coupled with shaft end portions of the traveling wheels through the universal joints.

The output gear 22a of the travel motor 22 meshes with the driven gear 25a, and the constant velocity joints 25 are coupled with the both ends of the shaft portion of the driven gear 25a.

The two traveling wheels 21a and 21b are arranged being inclined along the surface of the piping.

The constant velocity joints 25 are configured from the universal joints, thereby to allow the two traveling wheels 21a and 21b to be moved according to change of the surface shape of the piping and the like.

Sensors (an optical sensor, a limit switch, and the like) for recognizing operations, positions, and the like of the movable members may be arranged as needed.

The motors are remotely controlled by wired or wireless means.

When the motors are remotely controlled by wired means, a cable for supplying various signals from a controlling device (not illustrated) and power is connected. With the cable, the remote control of driving of the movable portions such as the traveling devices and the revolving member drive mechanism are possible. In addition, remote control of the neutron moisture meter as the inspection device is possible.

When the motors are remotely controlled by wireless means, a battery is mounted on an appropriate place of the main frame 1, and the battery is used as a power source.

(3) Revolving Member Drive Mechanism

The revolving member drive mechanisms D2 are mechanisms arranged on inner surfaces of the front and rear frame plates 11 and 12, and which hold and revolve the moisture measuring device 9 along the outer circumference of the piping P. For the revolving member drive mechanisms D2, FIGS. 6, 8, 10, and 11 can be mainly referred.

The revolving member drive mechanisms D2 couple the two revolving members 32 arranged on the inner surfaces of the front and rear frame plates 11 and 12 with revolving member beams 36, and arranges the moisture measuring device 9 between the revolving members in a movable manner.

The revolving member drive mechanism. D2 includes a group of the outside guide rolls 33a and a group of the inside guide rolls 33b having a two-line configuration that guides the revolving member 32, the drive motor 31 that revolves the revolving member 32, the drive gear 34 that receives transmission of power from a rotating shaft of a revolving motor, and the rack gear 35 provided on the revolving member 32 to mesh with the drive gear 34.

The drive motor 31 is remotely operated, the drive gear 34 is rotated, the revolving member 32 is revolved, and the attached moisture measuring device 9 is moved in the circumferential direction along the outer circumference of the piping P.

FIG. 10 illustrates a state in which the revolving member drive mechanism D2 is in an upper position, and FIG. 11 illustrates a state in which the revolving member drive mechanism D2 in a lower position.

When the revolving member drive mechanism D2 is in the position illustrated in FIG. 10, the moisture measuring device 9 faces the uppermost portion of the piping P, and can measure the moisture of the portion. Further, in the position of FIG. 11, the moisture measuring device 9 faces the lowermost portion of the piping P, and can measure the moisture of the portion. Further, in a moving path between the upper position of FIG. 10 and the lower position of FIG. 11, the moisture measuring device can measure the moisture of the outer circumferential surface of the piping P. Therefore, the moisture measuring device can measure the moisture of the entire circumference of the piping in total.

Note that a weight (counterweight) for securing weight balance is arranged to an appropriate position in the vicinity of the both end portions of the revolving members 32 in the circumferential direction, for example, to the revolving member beam 36a that couples the both end portions of the two revolving members in the circumferential direction, whereby stability of when the position of the center of gravity is moved as the revolving members are revolved and the moisture measuring device 9 is moved in the circumferential direction can be secured.

(4) Moisture Measuring Device

The moisture measuring device 9 is mainly illustrated in FIGS. 3, 4, 5, 7, 8, and 12. FIG. 3 is a plan view of the piping inspection robot A in a state of being placed on the piping P, and illustrates an attaching configuration of the moisture measuring device 9. In FIG. 8, the moisture measuring device 9 in a state where the revolving members are revolved to the lower position appears.

The moisture measuring device 9 is a device for measuring the amount of moisture contained between the pipe body and the heat insulating material wound around the pipe body, or the amount of moisture contained in the heat insulating material. The neutron moisture meter 91 radiates fast neutrons having high energy from a radiation source. The fast neutrons lose the energy when colliding with hydrogen atoms having the smallest mass, and become slow thermal neutrons. The change amount of the fast neutrons changed into the thermal neutrons is proportional to the amount of hydrogen in an object to be measured. The neutron moisture meter 91 includes a sensor that selectively detects only the thermal neutrons, and can measure the amount of moisture based on a detection amount of the thermal neutrons.

That is, the moisture measuring device 9 includes a housing (inspection device housing unit) 96 in which the neutron moisture meter 91 is built in, and the housing 96 is advanced/retracted by a measuring device drive mechanism D5 toward the circumferential surface of the piping P (in a diameter direction of the piping). An engagement piece (a member to be guided) slid and moved along the guides 93, and a rack gear 95 (FIG. 3) that meshes with a pinion gear 94 rotated and driven by the lifting and lowering motor 92 fixed to at least one of the revolving members and causing the moisture measuring device to advance/retract toward the surface of the piping are provided on a side surface 97 of the housing 96, the side surface 97 facing the revolving member 32 of the housing 96.

The lifting and lowering motor 92 is driven and the housing 96 is lowered, and the moisture measuring device is brought to come in contact with the piping P and measurement is performed. At non-measurement time, the moisture measuring device is lifted to a position where the moisture measuring device is not contact with the piping P. FIG. 12 (*a*) illustrates a state in which the moisture measuring device is in contact with the piping P, and FIG. 12 (*b*) illustrates a state in which the moisture measuring device is positioned (separated) at an upper position. A distance (space S) between the moisture measuring device and the piping when separated is set to about 10 mm.

The main frame 1 is stopped every time moved on the piping P in the longitudinal direction by 250 mm. Then, during the stop, the amount of moisture is measured and recorded by the neutron moisture meter 91. By repetition of such an operation, so that the amount of moisture of the heat insulating material of the piping P is measured.

When the neutron moisture meter 91 is installed on a top of the piping P, the amount of moisture in a range of ±35 degrees of the top of the piping in the circumferential direction is measured. Further, when the neutron moisture meter 91 is installed on a bottom of the piping, the amount of moisture in a range of ±35 degrees of the bottom of the piping is measured. This is because, from experience, it is known that rust is caused on the top or the bottom of the piping.

Note that a mechanism that can finely adjust positional relationship between the neutron moisture meter and the piping (interval I) in an up and down direction may be provided. With the mechanism, the amount of moisture can be more accurately measured. Further, in the present embodiment, the neutron moisture meter is housed in the housing 96, and the amount of moisture contained in the heat insulating material is measured. However, other measuring devices and flaw detection devices (a magnetic measuring device, an ultrasonic measuring device, and an X-ray measuring device) may be housed.

(5) Neutron Moisture Meter

Figure 13:
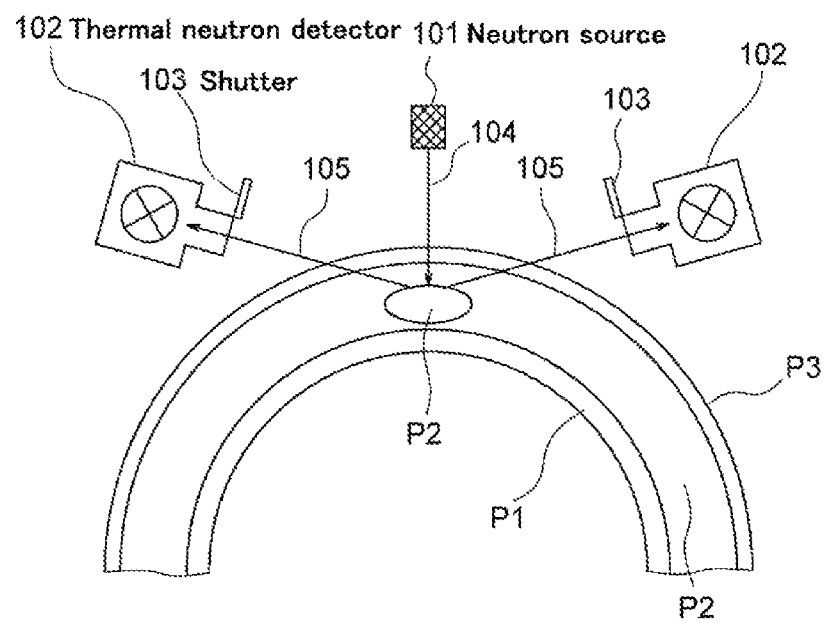
FIG. 13 is a diagram illustrating a principle of a moisture measuring device.

An outline of a moisture detection principle with the neutron moisture meter is illustrated in FIG. 13.

The neutron moisture meter detects thermal neutrons 105 with a thermal neutron detector 102. The thermal neutrons 105 are generated such that neutrons 104 radiated from a neutron source 101 lose energy by performing multiple elastic collision with hydrogen and the like in the moisture. The neutrons have a characteristic of easily transmitting elements with larger atomic numbers such as gold, and easily colliding with elements with smaller atomic numbers such as hydrogen. The neutrons that have repeated the collision lose the energy, and can be detected by the thermal neutron detector at a state where the neutrons decelerate to energy called thermal neutron. The neutron moisture meter is exemplified in Japanese Patent Application Laid-Open No. 2011-27559.

The piping has a laminate configuration in which the lagging material P2 is sandwiched between the steel pipe P1 and the metal-made covering material P3. The number of thermal neutrons generated when the neutrons collide with a hydrogen component, which is proportional to the amount of moisture contained in the lagging material P2, is changed. Therefore, the moisture is detected by detection of the thermal neutrons.

In the present invention, it is set that a thermal neutron-entering cylinder is inclined and the thermal neutrons generated from the detected portion of the lagging material is focused and captured. Then, the mechanism that lifts/lowers the neutron moisture meter is employed. Therefore, a shutter 103 is provided on the thermal neutron-entering cylinder in order to measure a position to be measured, measurement is performed in accordance with measurement timing, and the accuracy is improved. The measurement is performed in both of open and close states of the shutter, and a different between the two states is obtained, whereby information is detected only from the object to be measured.

(6) Operation

A measurement sequence is as follows.

(a) The piping inspection robot A is installed (placed) on an upper portion of the outer circumferential surface of an arbitrary position (for example, one end portion) of the piping P, and is caused to be in the state of FIGS. 1 to 7.

(b) The measuring device drive mechanism D5 is controlled, the neutron moisture meter 91 is moved toward the piping and is brought to come in contact with the piping outer surface. Appropriate positional relationship between the neutron moisture meter 91 and the circumferential surface of the piping is detected using sensors (not illustrated) such as a limit switch and a photo sensor (especially, a reflection type).

(c) The shutter 103 inside the neutron moisture meter is open and disturbance is measured (about for 15 seconds).

(d) The shutter 103 is closed, and measurement is started (about 15 seconds).

(f) A signal of measurement termination is confirmed.

(g) The measuring device drive mechanism D5 is controlled, and the neutron moisture meter is separated from the piping P.

(h) The piping inspection robot A is caused to travel by a predetermined distance (for example, 250 mm).

(i) The piping inspection robot is steered as needed and guided to another position on the piping.

Then, the processes from (b) to (h) are repeated, and the moisture is inspected in the length direction.

Note that minimum required processes in check work using the piping inspection robot of the present invention are a setting process of fitting the recessed part to the piping outer surface, a process of measuring existence or non-existence of the abnormality of the piping with the inspection device, a process of moving the inspection device in the circumferential direction of the piping and measuring the existence or non-existence of the abnormality of each portion of the piping of the circumferential direction, and a process of moving the inspection device in the axis direction of the piping.

When a lower portion of the piping P is inspected, the revolving member drive mechanism is revolved, and the neutron moisture meter is positioned at a lower position as illustrated in FIG. 8, and a similar measurement sequence is performed.

The present embodiment has a configuration of a piping inspection robot suitable for measurement of a horizontal piping (a horizontal portion of the piping).

Since the horizontal piping is supported by a T-shaped stand from below, the piping inspection robot can pass through the stand part in a state where the revolving members are rotated and the lower portion is open. Therefore, the horizontal portion of the piping can be inspected without any difficulty. The piping is arranged at a high place or in a complicated manner in a plant, a power station, or a nuclear power facility. Approach to the piping is difficult in an accident site. The present piping inspection robot can be controlled from a remote position.

Figure 14:
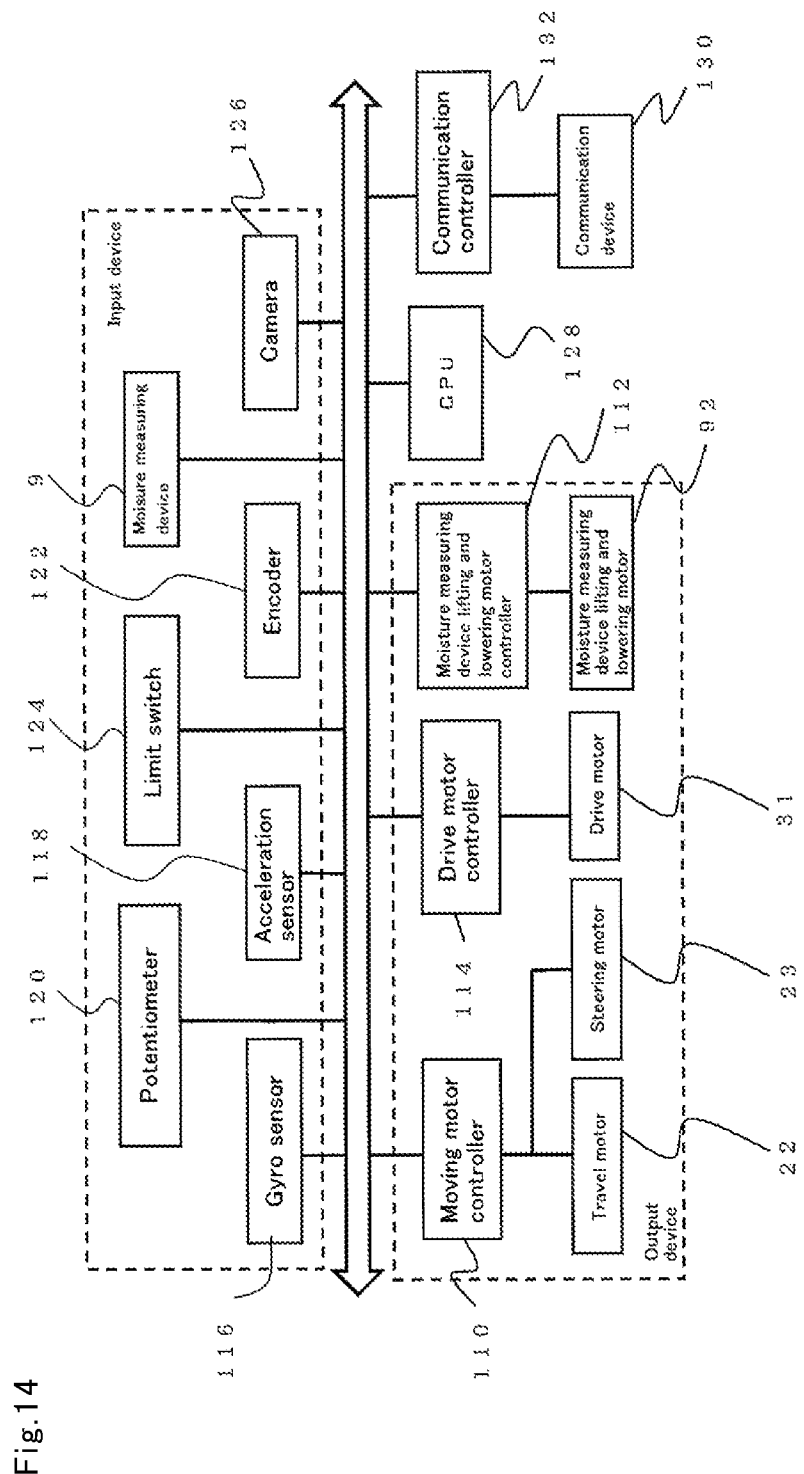
FIG. 14 is a diagram illustrating a control block of the piping inspection robot according to the present invention.

Next, FIG. 14 is a diagram illustrating a control block of the piping inspection robot according to the present invention. As output devices such as motors, the travel motor 22, the steering motor 23, a moving motor controller 110 that controls the travel motor 22 and the steering motor 23, the moisture measuring device lifting and lowering motor 92, a moisture measuring device lifting and lowering motor controller 112 that controls the moisture measuring device lifting and lowering motor 92, the drive motor 31, and a drive motor controller 114 that controls the drive motor 31.

Further, as input devices such as sensors, a gyro sensor 116 and an acceleration sensor 118 that control an attitude of the piping inspection robot, a potentiometer 120 that detects a rotation position of the revolving member driven by the drive motor 31, an encoder 122 for detecting a moved distance of the piping inspection device on the piping by driving of the travel motor 22, the moisture measuring device 9, a limit switch 124 that detects proximity of the moisture measuring device to the piping in a vertical direction, and a camera 126 for imaging an advancing direction or the vicinity of the advancing direction of the piping inspection device. Note that the encoder 122 is also provided in the moisture measuring device lifting and lowering motor 92, and detects the amount of rotation of the motor 92 together with the proximity detection with the limit switch 124.

Further, a CPU 128 for controlling the controllers and the input devices, and a communication device 130 and a communication controller 132 for transmitting collected data are included.

The piping inspection robot is moved on the piping that is an object to be inspected by driving the travel motor 22, the attitude of the piping inspection robot is detected with the gyro sensor 116 and the acceleration sensor 118, and when the piping inspection robot is moved being inclined from the uppermost portion of the piping in the circumferential direction when being moved in the axis direction of the piping, the deviation amount of the inclination is detected, and the steering motor 23 is controlled, whereby the piping inspection robot can be reliably moved in the vicinity of the uppermost portion of the piping in the circumferential direction.

Further, the moved distance of the piping inspection robot in the horizontal direction can be detected with the encoder 122 attached to the travel motor 22, whereby the moisture measurement can be conducted at a desired position.

After the piping inspection robot is moved to the desired position, the lifting and lowering motor 92 of the moisture measuring device is driven, the moisture measuring device 9 is brought to come close to the piping from an initial position, and the degree of proximity is detected by the limit switch 124, so that the moisture measuring device lifting and lowering motor controller 112 controls the lifting and lowering motor 92. Further, after the moisture measurement is terminated, the lifting and lowering motor 92 is driven again, and the moisture measuring device 9 is restored to the initial position. Note that, as control to restore the lifting and lowering motor 92 to the initial position, a potentiometer is attached to the moisture measuring device lifting and lowering motor, and an amount corresponding to the rotation amount of the lifting and lowering motor moved at the measurement may be employed as the moved amount for the restoration to the initial position. Further, although not illustrated, a proximity sensor for the moisture measuring device 9 is provided in the main frame 1, and when the proximity sensor detects the restoration to the initial position, control to stop the driving of the lifting and lowering motor 92 and the like may be performed.

Next, when the revolving members 32 are rotated for measuring the moisture of a lower side of the piping, the drive motors 31 are driven, and the rotated state is detected by an output of the potentiometer 120, whereby the moisture measuring device 9 attached to the revolving members can be arranged at a desired position.

The piping inspection robot controlled as described above performs the moisture measurement of the piping to be measured at a desired position, and transmits data obtained through the measurement to a PC or a server that performs data collection through the communication device 130.

The motors, the communication device, and the various sensors such as the moisture measuring device can be driven by a battery (not illustrated).

As described above, the piping inspection device according to the present invention includes the various sensors, performs movement and measurement based on the outputs of the sensors, and transmits the measured data to a remote center or the like through the communication device. Since the piping inspection device does not need wiring of power supply, it is not necessary to care about entanglement of wiring with a structure at the measuring position, and can independently perform data collection without troubling the worker.

Note that, in the above embodiment, a limit switch contact detection sensor has been used. However, a contactless detection sensor such as a position sensitive detector (PSD) may be used.

<Summary of the Configurations, Functions, and Effects of the Present Invention>

The piping inspection robot A according to the first present invention is means placed, coming in contact with, and coming close to the outer circumferential surface of the piping P, advanceable/retractable in the axis direction (longitudinal direction) of the piping, and which detects the existence or non-existence of the abnormality of the piping. The piping inspection robot A includes the main frame 1 including the recessed part 17 fit onto the outer circumferential surface of the piping, the main frame drive mechanism (first drive mechanism) D1 that causes the main frame to advance/retract in the axis direction of the piping, the revolving member 32 supported in an advanceable/retractable manner along the arc-shaped locus in the recessed part of the main frame, and the inspection device mounted on the revolving member.

The existence or non-existence of the abnormality (corrosion, wear, damage, fluid leakage of the piping) of portions of the piping of the circumferential direction can be detected and measured using the single piping inspection robot, whereby the work efficiency can be substantially enhanced.

That is, a conventional piping inspection robot cannot move the inspection device in the circumferential direction of the piping. Thus, to measure a circumferential surface portion other than a circumferential surface portion where the robot is arranged, there are only ways to set the robot to the piping again, or to set another robot. Therefore, the work efficiency was poor.

In contrast, in the present invention, not only is one piping inspection robot moved in the axis direction of the piping, but also can move the inspection device in the circumferential direction. Therefore, the inspection work efficiency can be substantially enhanced.

As the inspection device, any means can be applied as long as the means can measure deterioration, corrosion, damage, and wear of the piping, and fluid leakage inside the piping.

The present piping inspection robot is self-propelled on the piping, measures the moisture contained in the lagging material using a mounted inspection device, for example, the neutron moisture meter, and can detect risk of corrosion. The piping inspection robot can easily check and inspect the piping arranged in a place where a human cannot easily approach.

Further, the main body of the robot can reverse the inspection device, for example, the neutron moisture meter, in a state of being placed on the piping. Therefore, the moisture measuring device including the neutron moisture meter can be decreased in weight. As a result, the configuration devices such as a frame and a traveling mechanism can be decreased in weight. Therefore, a light piping inspection robot including a mechanism that can inspect an upper surface and a lower surface can be realized, and a load to the piping to be treated and inspected becomes small.

Since an open frame is used, the present piping inspection robot can be moved on the piping without being interrupted by the T-shaped piping support stand.

In the piping inspection robot according to the second present invention, the inspection device is configured to be freely advanceable/retractable in a direction intersecting with a moving direction of the revolving member.

Since the inspection device needs to come close to (in contact with) the piping outer surface at an inspection depending on a type of the inspection device, the inspection device is made advanceable/retractable with respect to the piping outer surface. When the inspection device can perform an inspection while maintaining a fixed distance from the piping, it is not necessary to be freely advanceable/retractable.

In the piping inspection robot according to the third present invention, the first drive mechanism D1 includes the movable base 5 pivotally supported in a freely revolvable manner in a direction intersecting with a moving direction of the main body, by a main frame portion corresponding to the central position of the recessed part 17, the movable base drive mechanism (third drive mechanism) D3 that changes the revolution angle of the movable base, the pair of traveling wheels 21a and 21b supported by the movable base in a freely rotatable manner, and the wheel drive mechanism (fourth drive mechanism) D4 that rotates and drives the traveling wheels. The pair of traveling wheels is arranged symmetrically with respect to the shaft portion 5a of the movable base as a center.

The traveling stability of the traveling wheels supported by the movable base 5 in a freely rotatable manner cannot be impaired due to change of the shape of the outer surface of the piping and the like because the movable base can be turned in the horizontal direction and other intersecting directions around the shaft portion 5a. That is, the traveling wheels can be rotated while being turned and revolved corresponding to condition change of the piping outer surface.

In the piping inspection robot according to the fourth present invention, the movable base 5 is pivotally supported in a freely revolvable manner by the shaft portion 5a perpendicular to a tangential line assumed on the outer circumferential surface of the piping facing the central position of the recessed part 17.

The central position of the recessed part 17 is a center portion of the arc-shaped recessed portion 14 in the circumferential direction, and the movable base 5 is pivotally supported by the shaft portion 5a arranged at the position in a freely revolvable manner in the intersecting direction, whereby the right and left traveling wheels can be caused to travel on the piping with a well-balanced and stable manner.

In the piping inspection robot according to the fifth present invention, the fourth drive mechanism D4 includes the travel motor 22 mounted on the movable base, the driven gear 25a supported by the movable base in a freely rotatable manner, and which receives transmission of drive force from the output gear of the travel motor, and the universal joints 25 respectively coupled with the both end portions of the rotating shaft of the driven gear. The fourth drive mechanism D4 is coupled with the shaft end portions of the traveling wheels through the universal joints.

The angle of the rotating shaft of the traveling wheels can further changed with the universal joints. Therefore, the right and left traveling wheels can travel on the piping in a well-balanced and stable manner.

The inspection device according to the sixth present invention is any one of the moisture measuring device including the neutron moisture meter, the ultrasonic flaw detection device, the magnetic flaw detection device, and the X-ray flaw detection device.

As the inspection device, any means can be employed as long as the means can detect the abnormality of the piping.

In the piping inspection robot according to the seventh present invention, the drive mechanisms are remotely operated by wireless or wired means.

When the drive mechanisms are driven by the wireless means, a battery is mounted as a power source. In the case of the wired means, the power and the signals are supplied using a cable.

The inspection method using the piping inspection robot according to the eighth present invention is the method of inspecting piping using the piping inspection robot according to claims 1 to 7, and the method includes the setting process of fitting the recessed part onto the piping outer surface, the process of measuring the existence or non-existence of the abnormality of the piping with the inspection device, the process of moving the inspection device in the circumferential direction of the piping and measuring the existence or non-existence of the abnormality of portions of the piping of the circumferential direction, and the process of moving the inspection device in the axis direction of the piping.

By conductance of the minimum required processes above, the entire outer surface of the piping can be efficiently inspected using the inspection device.

The piping is arranged at a high place or in a complicated manner in a plant, a power station, or a nuclear power facility. Further, approach to the piping is difficult in an accident site of such a facility. The present piping inspection robot can be controlled from a remote position, and is suitable for a check of the piping arranged in the horizontal direction.

The method of inspecting piping according to the ninth present invention is the method of inspecting piping according to claim 8 using the moisture measuring device as the inspection device, and the method causes the moisture measuring device to come close to the piping at the time of measurement, and causes the moisture measuring device to be separated from the piping at the time of non-measurement.

An inspection of the piping by different techniques can be performed by mounting of various inspection devices on the single piping inspection robot. When the moisture measuring device is used as the inspection device, it is favorable to configure the inspection device in a freely advanceable/retractable manner with respect to the piping outer surface in order to enhance the detection accuracy.

In the measurement sequence, (1) the piping inspection robot is placed on the piping, (2) the neutron moisture meter is lowered by the lifting and lowering device, and is brought to come in contact with the piping, (3) the shutter of the neutron moisture meter is open and the thermal neutrons are measured, (4) the shutter is closed and the thermal neutrons are measured, (5) the signal of measurement termination is confirmed, (6) the moisture meter is lifted by the lifting and lowering device and is separated from the piping, (7) the robot is caused to travel by a predetermined distance (about 250 mm), and (8) the robot is steered as needed and is guided to the center of the piping. Then, the processes of (2) to (8) are repeated, and the moisture is inspected in the length direction. Further, the revolving member is rotated and the moisture measuring device is moved to the lower surface side of the piping, the processes of (2) to (8) are repeated, and the lower surface of the piping is inspected in the longitudinal direction.

Note that the reason why the two states of the open and close of the shutter are measured is that a different between the two states are measured as the thermal neutron amount from the object to be inspected, and the accuracy is improved.

Accordingly, the amount of moisture contained in the lagging material can be detected on the upper and lower surfaces of the piping at predetermined intervals in the length direction.

INDUSTRIAL APPLICABILITY

According to the present piping inspection robot, nondestructive diagnosis of the existence or non-existence of damage, fluid leakage, and the like of the piping in a high position or in an intricate place can be performed while the piping inspection robot is controlled from a remote position. The piping inspection robot is suitable for an inspection of the piping arranged in a high place or in a complicated manner, in a chemical plant, a power station, or a nuclear power facility. Especially, the piping inspection robot is effective in an accident site of a nuclear facility where approach is difficult.

REFERENCE SIGNS LIST

1 . . . main frame, 11 . . . front frame plate, 11a . . . recessed portion, 11b . . . fixed member, 12 . . . rear frame plate, 12a . . . recessed portion, 12b . . . fixed member, 13 . . . beam material, 14 . . . arc-shaped recessed portion, 15 . . . linear portion, 16 . . . lower end, 17 . . . recessed part, 2 . . . traveling device, 21a . . . traveling wheel, 22 . . . travel motor, 23 . . . steering motor, 23a . . . output gear, 24 . . . steering shaft, 25 . . . constant velocity joint (universal joint), 31 . . . drive motor, 32 . . . revolving member, 33a . . . guide roll, 33b . . . guide roll, 34 . . . drive gear, 35 . . . rack gear, 36 . . . revolving member beam, 5 . . . movable base, 5a . . . shaft portion, 5b . . . movable base driven gear, 9 . . . moisture measuring device, 91 . . . neutron moisture meter, 92 . . . lifting and lowering motor, 93 . . . guide, 94 . . . pinion gear, 94 . . . output gear, 95 . . . rack gear, 96 . . . housing, 97 . . . side surface, 101 . . . neutron source, 102 . . . thermal neutron detector, 103 . . . shutter, 104 . . . neutron, 105 . . . thermal neutron, A . . . piping inspection robot, D1 . . . main frame drive mechanism (first drive mechanism), D2 . . . revolving member drive mechanism (second drive mechanism), D3 . . . movable base drive mechanism (third drive mechanism), D4 . . . wheel drive mechanism (fourth drive mechanism), D5 . . . measuring device drive mechanism (fifth drive mechanism), P . . . piping, P1 . . . steel pipe (metal pipe body), P2 . . . lagging material, P3 . . . covering material, S . . . space

The invention claimed is:

1. A piping inspection robot placed on an outer circumferential surface of piping, advanceable/retractable in an axis direction of the piping, and which inspects existence or non-existence of abnormality of the piping, the piping inspection robot comprising:
a main frame including a recessed part fit onto the outer circumferential surface of the piping;
a main frame drive mechanism configured to cause the main frame to advance/retract in the axis direction of the piping;
a revolving member supported in a advanceable/retractable manner along an arc-shaped locus in the recessed part of the main frame;
a revolving member drive mechanism configured to move the revolving member; and
an inspection device mounted on the revolving member.

2. The piping inspection robot according to claim 1, wherein the inspection device is configured to be freely advanceable/retractable in a direction intersecting with a moving direction of the revolving member.

3. The piping inspection robot according to claim 1, wherein the main frame drive mechanism includes
a movable base pivotally supported in a freely revolvable manner in a direction intersecting with a moving direction of the main frame, by a portion of the main frame corresponding to a central position of the recessed part,
a movable base drive mechanism that changes a revolution angle of the movable base,
a pair of traveling wheels supported by the movable base in a freely rotatable manner,
a wheel drive mechanism that rotates and drives the traveling wheels, and
the pair of traveling wheels is arranged symmetrically with respect to a shaft portion of the movable base as a center.

4. The piping inspection robot according to claim 1, wherein the movable base is pivotally supported in a freely revolvable manner by the shaft portion perpendicular to a tangential line assumed on the outer circumferential surface of the piping facing the central position of the recessed part.

5. The piping inspection robot according to claim 1, wherein the wheel drive mechanism includes
a travel motor mounted on the movable base,
a driven gear supported by the movable base in a freely rotatable manner, and which receives transmission of drive force from an output gear of the travel motor,
universal joints respectively coupled with both end portions of a rotating shaft of the driven gear, and the wheel drive mechanism is coupled with shaft end portions of the traveling wheels through the universal joints.

6. The piping inspection robot according to claim 1, wherein the inspection device is any of a moisture measuring device including a neutron moisture meter, an ultrasonic flaw detection device, a magnetic flaw detection device, and an X-ray flaw detection device.

7. The piping inspection robot according to claim 1, wherein the drive mechanisms are remotely operated by wireless or wire communication.

8. A method of inspecting piping using the piping inspection robot according to claim 1, the method comprising:
- a setting process of fitting the recessed part onto the piping outer surface;
- a process of measuring existence or non-existence of abnormality of the piping by the inspection device;
- a process of moving the inspection device in a circumferential direction of the piping and measuring the existence or non-existence of abnormality of each portion of the piping of the circumferential direction; and
- a process of moving the inspection device in an axis direction of the piping.

9. The method of inspecting piping according to claim 8 using the moisture measuring device as the inspection device, the method causing the moisture measuring device to come close to the piping at a time of measurement, and causing the moisture measuring device to be separated from the piping at a time of non-measurement.

* * * * *